(12) United States Patent
Emmons et al.

(10) Patent No.: US 11,096,610 B2
(45) Date of Patent: Aug. 24, 2021

(54) SURGICAL IMPLANTS INCLUDING SENSING FIBERS

(71) Applicant: Covidien LP, Mansfield, MA (US)

(72) Inventors: Clifford L. Emmons, Dennis, MA (US); Seok Joo Chang, Seoul (KR); Hoon Cho, Seoul (KR)

(73) Assignee: COVIDIEN LP, Mansfield, MA (US)

( * ) Notice: Subject to any disclaimer, the term of this patent is extended or adjusted under 35 U.S.C. 154(b) by 381 days.

(21) Appl. No.: 15/892,551

(22) Filed: Feb. 9, 2018

(65) Prior Publication Data

US 2018/0279925 A1 Oct. 4, 2018

Related U.S. Application Data

(60) Provisional application No. 62/599,232, filed on Dec. 15, 2017, provisional application No. 62/477,458, filed on Mar. 28, 2017.

(51) Int. Cl.
*A61B 17/072* (2006.01)
*A61B 5/1459* (2006.01)
(Continued)

(52) U.S. Cl.
CPC ............ *A61B 5/1459* (2013.01); *A61B 5/076* (2013.01); *A61B 5/14539* (2013.01); *A61B 5/686* (2013.01); *A61B 17/07292* (2013.01); *A61B 90/06* (2016.02); *A61B 5/14546* (2013.01); *A61B 17/07207* (2013.01); *A61B 17/1155* (2013.01); *A61B 2017/00026* (2013.01); *A61B 2017/00035* (2013.01);
(Continued)

(58) Field of Classification Search
None
See application file for complete search history.

(56) References Cited

U.S. PATENT DOCUMENTS

| 3,054,406 A | 9/1962 | Usher |
| 3,079,606 A | 3/1963 | Bobrov et al. |

(Continued)

FOREIGN PATENT DOCUMENTS

| AU | 2012203630 A1 | 7/2012 |
| CA | 2282761 A1 | 9/1998 |

(Continued)

OTHER PUBLICATIONS

Extended European Search Report corresponding to EP Application No. 18164142.4, completed Jan. 14, 2019 and dated Jan. 22, 2019; (13 pp).

(Continued)

*Primary Examiner* — Eric F Winakur
*Assistant Examiner* — Marjan Fardanesh

(57) ABSTRACT

A monitoring system includes a surgical implant configured for implantation in vivo and having at least one sensing fiber configured to measure a preselected physiological parameter, and a receiving unit in wireless communication with the at least one sensing fiber and configured to receive measurements of the preselected physiological parameter. A surgical system includes an end effector having a plurality of fasteners, and a surgical implant securable to tissue via the plurality of fasteners. The surgical implant includes at least one sensing fiber configured to measure a preselected physiological parameter.

9 Claims, 6 Drawing Sheets

(51) Int. Cl.
*A61B 90/00* (2016.01)
*A61B 5/07* (2006.01)
*A61B 5/145* (2006.01)
*A61B 5/00* (2006.01)
A61B 17/00 (2006.01)
A61B 17/115 (2006.01)

(52) U.S. Cl.
CPC ............... *A61B 2017/00084* (2013.01); *A61B 2017/00221* (2013.01); *A61B 2017/07257* (2013.01); *A61B 2017/07271* (2013.01); *A61B 2090/064* (2016.02); *A61B 2562/0233* (2013.01)

(56) References Cited

U.S. PATENT DOCUMENTS

| | | |
|---|---|---|
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |
| 3,797,494 A | 3/1974 | Zaffaroni |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,112,496 A | 5/1992 | Dhawan et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,281,197 A | 1/1994 | Arias et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,370,650 A | 12/1994 | Tovey et al. |
| 5,392,979 A | 2/1995 | Green et al. |
| 5,397,324 A | 3/1995 | Carroll et al. |
| 5,405,072 A | 4/1995 | Zlock et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,645,915 A | 7/1997 | Kranzler et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,871,135 A | 2/1999 | Williamson, IV et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,957,363 A | 9/1999 | Heck |
| 5,964,394 A | 10/1999 | Robertson |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,142,933 A | 11/2000 | Longo et al. |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,270,530 B1 | 8/2001 | Eldridge et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,330,965 B1 | 12/2001 | Milliman et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,568,398 B2 | 5/2003 | Cohen |
| 6,590,095 B1 | 7/2003 | Schleicher et al. |
| 6,592,597 B2 | 7/2003 | Grant et al. |
| 6,605,294 B2 | 8/2003 | Sawhney |
| 6,610,006 B1 | 8/2003 | Amid et al. |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |

(56) References Cited

U.S. PATENT DOCUMENTS

| | | |
|---|---|---|
| 6,669,735 B1 | 12/2003 | Pelissier |
| 6,673,093 B1 | 1/2004 | Sawhney |
| 6,677,258 B2 | 1/2004 | Carroll et al. |
| 6,685,714 B2 | 2/2004 | Rousseau |
| 6,702,828 B2 | 3/2004 | Whayne |
| 6,703,047 B2 | 3/2004 | Sawhney et al. |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,746,869 B2 | 6/2004 | Pui et al. |
| 6,764,720 B2 | 7/2004 | Pui et al. |
| 6,773,458 B1 | 8/2004 | Brauker et al. |
| 6,818,018 B1 | 11/2004 | Sawhney |
| 6,843,252 B2 | 1/2005 | Harrison et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,953,139 B2 | 10/2005 | Milliman et al. |
| 6,959,851 B2 | 11/2005 | Heinrich |
| 7,009,034 B2 | 3/2006 | Pathak et al. |
| 7,025,772 B2 | 4/2006 | Gellman et al. |
| 7,060,087 B2 | 6/2006 | DiMatteo et al. |
| 7,087,065 B2 | 8/2006 | Ulmsten et al. |
| 7,106,043 B1 * | 9/2006 | Da Silva ............ A61B 5/6848 324/72.5 |
| 7,108,701 B2 | 9/2006 | Evens et al. |
| 7,128,253 B2 | 10/2006 | Mastri et al. |
| 7,128,748 B2 | 10/2006 | Mooradian et al. |
| 7,134,438 B2 | 11/2006 | Makower et al. |
| 7,141,055 B2 | 11/2006 | Abrams et al. |
| 7,147,138 B2 | 12/2006 | Shelton, IV |
| 7,160,299 B2 | 1/2007 | Baily |
| 7,179,268 B2 | 2/2007 | Roy et al. |
| 7,210,810 B1 | 5/2007 | Iversen et al. |
| 7,214,727 B2 | 5/2007 | Kwon et al. |
| 7,229,452 B2 | 6/2007 | Kayan |
| 7,232,449 B2 | 6/2007 | Sharkawy et al. |
| 7,241,300 B2 | 7/2007 | Sharkawy et al. |
| 7,247,338 B2 | 7/2007 | Pui et al. |
| 7,279,322 B2 | 10/2007 | Pui et al. |
| 7,307,031 B2 | 12/2007 | Carroll et al. |
| 7,308,998 B2 | 12/2007 | Mastri et al. |
| 7,311,720 B2 | 12/2007 | Mueller et al. |
| 7,328,829 B2 | 2/2008 | Arad et al. |
| 7,334,717 B2 | 2/2008 | Rethy et al. |
| 7,347,850 B2 | 3/2008 | Sawhney |
| 7,377,928 B2 | 5/2008 | Zubik et al. |
| 7,434,717 B2 | 10/2008 | Shelton, IV et al. |
| 7,438,209 B1 | 10/2008 | Hess |
| 7,464,849 B2 | 12/2008 | Shelton, IV et al. |
| 7,498,063 B2 | 3/2009 | Pui et al. |
| 7,547,312 B2 | 6/2009 | Bauman et al. |
| 7,559,937 B2 | 7/2009 | de la Torre et al. |
| 7,571,845 B2 | 8/2009 | Viola |
| 7,592,418 B2 | 9/2009 | Pathak et al. |
| 7,594,921 B2 | 9/2009 | Browning |
| 7,595,392 B2 | 9/2009 | Kumar et al. |
| 7,604,151 B2 | 10/2009 | Hess et al. |
| 7,611,494 B2 | 11/2009 | Campbell et al. |
| 7,635,073 B2 | 12/2009 | Heinrich |
| 7,645,874 B2 | 1/2010 | Saferstein et al. |
| 7,649,089 B2 | 1/2010 | Kumar et al. |
| 7,655,288 B2 | 2/2010 | Bauman et al. |
| 7,662,409 B2 | 2/2010 | Masters |
| 7,662,801 B2 | 2/2010 | Kumar et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,673,782 B2 | 3/2010 | Hess et al. |
| 7,708,180 B2 | 5/2010 | Murray et al. |
| 7,709,631 B2 | 5/2010 | Harris et al. |
| 7,717,313 B2 | 5/2010 | Criscuolo et al. |
| 7,722,642 B2 | 5/2010 | Williamson, IV et al. |
| 7,735,703 B2 | 6/2010 | Morgan et al. |
| 7,744,627 B2 | 6/2010 | Orban, III et al. |
| 7,754,002 B2 | 7/2010 | Maase et al. |
| 7,776,060 B2 | 8/2010 | Mooradian et al. |
| 7,789,889 B2 | 9/2010 | Zubik et al. |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,866,526 B2 | 1/2011 | Green et al. |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban, III et al. |
| 7,951,248 B1 | 5/2011 | Fallis et al. |
| 7,967,179 B2 | 6/2011 | Olson et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,177 B2 | 9/2011 | Bettuchi et al. |
| 8,016,178 B2 | 9/2011 | Olson et al. |
| 8,025,199 B2 | 9/2011 | Whitman et al. |
| 8,028,883 B2 | 10/2011 | Stopek |
| 8,033,483 B2 | 10/2011 | Fortier et al. |
| 8,033,983 B2 | 10/2011 | Chu et al. |
| 8,038,045 B2 | 10/2011 | Bettuchi et al. |
| 8,062,330 B2 | 11/2011 | Prommersberger et al. |
| 8,062,673 B2 | 11/2011 | Figuly et al. |
| 8,083,119 B2 | 12/2011 | Prommersberger |
| 8,091,756 B2 | 1/2012 | Viola |
| 8,123,766 B2 | 2/2012 | Bauman et al. |
| 8,123,767 B2 | 2/2012 | Bauman et al. |
| 8,127,975 B2 | 3/2012 | Olson et al. |
| 8,133,336 B2 | 3/2012 | Kettlewell et al. |
| 8,133,559 B2 | 3/2012 | Lee et al. |
| 8,146,791 B2 | 4/2012 | Bettuchi et al. |
| 8,152,777 B2 | 4/2012 | Campbell et al. |
| 8,157,149 B2 | 4/2012 | Olson et al. |
| 8,157,151 B2 | 4/2012 | Ingmanson et al. |
| 8,167,895 B2 | 5/2012 | D'Agostino et al. |
| 8,177,797 B2 | 5/2012 | Shimoji et al. |
| 8,178,746 B2 | 5/2012 | Hildeberg et al. |
| 8,192,460 B2 | 6/2012 | Orban, III et al. |
| 8,201,720 B2 | 6/2012 | Hessler |
| 8,210,414 B2 | 7/2012 | Bettuchi et al. |
| 8,210,453 B2 | 7/2012 | Hull et al. |
| 8,216,272 B2 | 7/2012 | Shipp |
| 8,225,799 B2 | 7/2012 | Bettuchi |
| 8,225,981 B2 | 7/2012 | Criscuolo et al. |
| 8,231,043 B2 | 7/2012 | Tarinelli et al. |
| 8,235,273 B2 | 8/2012 | Olson et al. |
| 8,245,901 B2 | 8/2012 | Stopek |
| 8,252,339 B2 | 8/2012 | Figuly et al. |
| 8,252,921 B2 | 8/2012 | Vignon et al. |
| 8,256,654 B2 | 9/2012 | Bettuchi et al. |
| 8,257,391 B2 | 9/2012 | Orban, III et al. |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,317,790 B2 | 11/2012 | Bell et al. |
| 8,317,808 B2 | 11/2012 | Levin et al. |
| 8,322,590 B2 | 12/2012 | Patel et al. |
| 8,348,126 B2 | 1/2013 | Olson et al. |
| 8,348,130 B2 | 1/2013 | Shah et al. |
| 8,365,972 B2 | 2/2013 | Aranyi et al. |
| 8,367,089 B2 | 2/2013 | Wan et al. |
| 8,371,491 B2 | 2/2013 | Huitema et al. |

(56) References Cited

U.S. PATENT DOCUMENTS

| | | |
|---|---|---|
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,393,514 B2 | 3/2013 | Shelton, IV et al. |
| 8,393,517 B2 | 3/2013 | Milo |
| 8,408,440 B2 | 4/2013 | Olson et al. |
| 8,408,480 B2 | 4/2013 | Hull et al. |
| 8,413,869 B2 | 4/2013 | Heinrich |
| 8,413,871 B2 | 4/2013 | Racenet et al. |
| 8,418,909 B2 | 4/2013 | Kostrzewski |
| 8,424,742 B2 | 4/2013 | Bettuchi |
| 8,453,652 B2 | 6/2013 | Stopek |
| 8,453,904 B2 | 6/2013 | Eskaros et al. |
| 8,453,909 B2 | 6/2013 | Olson et al. |
| 8,453,910 B2 | 6/2013 | Bettuchi et al. |
| 8,464,925 B2 | 6/2013 | Hull et al. |
| 8,470,360 B2 | 6/2013 | McKay |
| 8,474,677 B2 | 7/2013 | Woodard, Jr. et al. |
| 8,479,968 B2 | 7/2013 | Hodgkinson et al. |
| 8,485,414 B2 | 7/2013 | Criscuolo et al. |
| 8,496,683 B2 | 7/2013 | Prommersberger et al. |
| 8,511,533 B2 | 8/2013 | Viola et al. |
| 8,512,402 B2 | 8/2013 | Marczyk et al. |
| 8,518,440 B2 | 8/2013 | Blaskovich et al. |
| 8,529,600 B2 | 9/2013 | Woodard, Jr. et al. |
| 8,540,128 B2 | 9/2013 | Shelton, IV et al. |
| 8,540,131 B2 | 9/2013 | Swayze |
| 8,551,138 B2 | 10/2013 | Orban, III et al. |
| 8,556,918 B2 | 10/2013 | Bauman et al. |
| 8,561,873 B2 | 10/2013 | Ingmanson et al. |
| 8,579,990 B2 | 11/2013 | Priewe |
| 8,584,920 B2 | 11/2013 | Hodgkinson |
| 8,590,762 B2 | 11/2013 | Hess et al. |
| 8,616,430 B2 | 12/2013 | (Prommersberger) Stopek et al. |
| 8,617,132 B2 | 12/2013 | Golzarian et al. |
| 8,631,989 B2 | 1/2014 | Aranyi et al. |
| 8,646,674 B2 | 2/2014 | Schulte et al. |
| 8,668,129 B2 | 3/2014 | Olson |
| 8,678,263 B2 | 3/2014 | Viola |
| 8,679,137 B2 | 3/2014 | Bauman et al. |
| 8,684,250 B2 | 4/2014 | Bettuchi et al. |
| 8,701,958 B2 | 4/2014 | Shelton, IV et al. |
| 8,721,703 B2 | 5/2014 | Fowler |
| 8,727,197 B2 | 5/2014 | Hess et al. |
| 8,757,466 B2 | 6/2014 | Olson et al. |
| 8,789,737 B2 | 7/2014 | Hodgkinson et al. |
| 8,814,888 B2 | 8/2014 | Sgro |
| 8,820,606 B2 | 9/2014 | Hodgkinson |
| 8,827,133 B2 | 9/2014 | Shelton, IV et al. |
| 8,857,694 B2 | 10/2014 | Shelton, IV et al. |
| 8,864,009 B2 | 10/2014 | Shelton, IV et al. |
| 8,870,050 B2 | 10/2014 | Hodgkinson |
| 8,906,045 B2 | 12/2014 | Levin et al. |
| 8,920,443 B2 | 12/2014 | Hiles et al. |
| 8,920,444 B2 | 12/2014 | Hiles et al. |
| 8,939,344 B2 | 1/2015 | Olson et al. |
| 8,956,390 B2 | 2/2015 | Shah et al. |
| 8,967,448 B2 | 3/2015 | Carter et al. |
| 9,005,243 B2 | 4/2015 | Stopek et al. |
| 9,010,606 B2 | 4/2015 | Aranyi et al. |
| 9,010,608 B2 | 4/2015 | Casasanta, Jr. et al. |
| 9,010,609 B2 | 4/2015 | Carter et al. |
| 9,010,610 B2 | 4/2015 | Hodgkinson |
| 9,010,612 B2 | 4/2015 | Stevenson et al. |
| 9,016,543 B2 | 4/2015 | (Prommersberger) Stopek et al. |
| 9,016,544 B2 | 4/2015 | Hodgkinson et al. |
| 9,027,817 B2 | 5/2015 | Milliman et al. |
| 9,044,227 B2 | 6/2015 | Shelton, IV et al. |
| 9,055,944 B2 | 6/2015 | Hodgkinson et al. |
| 9,084,602 B2 | 7/2015 | Gleiman |
| 9,107,665 B2 | 8/2015 | Hodgkinson et al. |
| 9,107,667 B2 | 8/2015 | Hodgkinson |
| 9,107,726 B2 | 8/2015 | Levin et al. |
| 9,113,871 B2 | 8/2015 | Milliman et al. |
| 9,113,873 B2 | 8/2015 | Marczyk et al. |
| 9,113,885 B2 | 8/2015 | Hodgkinson et al. |
| 9,113,893 B2 | 8/2015 | Sorrentino et al. |
| 9,161,753 B2 | 10/2015 | Prior |
| 9,161,757 B2 | 10/2015 | Bettuchi |
| 9,186,140 B2 | 11/2015 | Hiles et al. |
| 9,186,144 B2 | 11/2015 | Stevenson et al. |
| 9,192,378 B2 | 11/2015 | Aranyi et al. |
| 9,192,379 B2 | 11/2015 | Aranyi et al. |
| 9,192,380 B2 | 11/2015 | (Tarinelli) Racenet et al. |
| 9,192,383 B2 | 11/2015 | Milliman |
| 9,192,384 B2 | 11/2015 | Bettuchi |
| 9,198,660 B2 | 12/2015 | Hodgkinson |
| 9,198,663 B1 | 12/2015 | Marczyk et al. |
| 9,204,881 B2 | 12/2015 | Penna |
| 9,220,504 B2 | 12/2015 | Viola et al. |
| 9,226,754 B2 | 1/2016 | D'Agostino et al. |
| 9,237,892 B2 | 1/2016 | Hodgkinson |
| 9,237,893 B2 | 1/2016 | Carter et al. |
| 9,277,922 B2 | 3/2016 | Carter et al. |
| 9,295,466 B2 | 3/2016 | Hodgkinson et al. |
| 9,326,768 B2 | 5/2016 | Shelton, IV |
| 9,326,773 B2 | 5/2016 | Casasanta, Jr. et al. |
| 9,328,111 B2 | 5/2016 | Zhou et al. |
| 9,345,479 B2 | 5/2016 | (Tarinelli) Racenet et al. |
| 9,351,729 B2 | 5/2016 | Orban, III et al. |
| 9,351,731 B2 | 5/2016 | Carter et al. |
| 9,351,732 B2 | 5/2016 | Hodgkinson |
| 9,358,005 B2 | 6/2016 | Shelton, IV et al. |
| 9,364,229 B2 | 6/2016 | D'Agostino et al. |
| 9,364,234 B2 | 6/2016 | (Prommersberger) Stopek et al. |
| 9,386,988 B2 | 7/2016 | Baxter, III et al. |
| 9,402,627 B2 | 8/2016 | Stevenson et al. |
| 9,414,839 B2 | 8/2016 | Penna |
| 9,433,412 B2 | 9/2016 | Bettuchi et al. |
| 9,433,413 B2 | 9/2016 | Stopek |
| 9,433,420 B2 | 9/2016 | Hodgkinson |
| 9,445,812 B2 | 9/2016 | Olson et al. |
| 9,445,817 B2 | 9/2016 | Bettuchi |
| 9,463,260 B2 | 10/2016 | Stopek |
| 9,486,215 B2 | 11/2016 | Olson et al. |
| 9,492,170 B2 | 11/2016 | Bear et al. |
| 9,504,470 B2 | 11/2016 | Milliman |
| 9,517,164 B2 | 12/2016 | Vitaris et al. |
| 9,572,576 B2 | 2/2017 | Hodgkinson et al. |
| 9,585,657 B2 | 3/2017 | Shelton, IV et al. |
| 9,597,077 B2 | 3/2017 | Hodgkinson |
| 9,610,080 B2 | 4/2017 | Whitfield et al. |
| 9,622,745 B2 | 4/2017 | Ingmanson et al. |
| 9,629,626 B2 | 4/2017 | Soltz et al. |
| 9,636,850 B2 | 5/2017 | Stopek (nee Prommersberger) et al. |
| 9,655,620 B2 | 5/2017 | Prescott et al. |
| 9,655,709 B2 | 5/2017 | Kelly et al. |
| 9,675,351 B2 | 6/2017 | Hodgkinson et al. |
| 9,681,936 B2 | 6/2017 | Hodgkinson et al. |
| 9,687,262 B2 | 6/2017 | Rousseau et al. |
| 9,693,772 B2 | 7/2017 | Ingmanson et al. |
| 9,708,184 B2 | 7/2017 | Chan et al. |
| 9,770,245 B2 | 9/2017 | Swayze et al. |
| 9,775,617 B2 | 10/2017 | Carter et al. |
| 9,775,618 B2 | 10/2017 | Bettuchi et al. |
| 9,782,173 B2 | 10/2017 | Mozdzierz |
| 9,844,378 B2 | 12/2017 | Casasanta et al. |
| 2002/0091397 A1 | 7/2002 | Chen |
| 2002/0151911 A1 | 10/2002 | Gabbay |
| 2003/0065345 A1 | 4/2003 | Weadock |
| 2003/0078209 A1 | 4/2003 | Schmidt |
| 2003/0083676 A1 | 5/2003 | Wallace |
| 2003/0125676 A1 | 7/2003 | Swenson et al. |
| 2003/0181927 A1 | 9/2003 | Wallace |
| 2003/0208231 A1 | 11/2003 | Williamson et al. |
| 2004/0092912 A1 | 5/2004 | Jinno et al. |
| 2004/0107006 A1 | 6/2004 | Francis et al. |
| 2004/0131418 A1 | 7/2004 | Budde et al. |
| 2004/0236192 A1 | 11/2004 | Necola Shehada et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |

(56) References Cited

U.S. PATENT DOCUMENTS

| | | |
|---|---|---|
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0149073 A1 | 7/2005 | Arani et al. |
| 2005/0283256 A1 | 12/2005 | Sommerich et al. |
| 2006/0008505 A1 | 1/2006 | Brandon |
| 2006/0121266 A1 | 6/2006 | Fandel et al. |
| 2006/0173470 A1 | 8/2006 | Oray et al. |
| 2006/0190027 A1 | 8/2006 | Downey |
| 2006/0235500 A1 | 10/2006 | Gibson et al. |
| 2007/0034669 A1 | 2/2007 | de la Torre et al. |
| 2007/0203510 A1 | 8/2007 | Bettuchi |
| 2007/0243227 A1 | 10/2007 | Gertner |
| 2007/0246505 A1 | 10/2007 | Pace-Floridia et al. |
| 2008/0009811 A1 | 1/2008 | Cantor |
| 2008/0029570 A1 | 2/2008 | Shelton et al. |
| 2008/0033569 A1 | 2/2008 | Ferren et al. |
| 2008/0082126 A1 | 4/2008 | Murray et al. |
| 2008/0140115 A1 | 6/2008 | Stopek |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0216855 A1 | 9/2008 | Nasca |
| 2008/0220047 A1 | 9/2008 | Sawhney et al. |
| 2008/0290134 A1 | 11/2008 | Bettuchi et al. |
| 2009/0001121 A1 | 1/2009 | Hess et al. |
| 2009/0001130 A1 | 1/2009 | Hess et al. |
| 2009/0031842 A1 | 2/2009 | Kawai et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0218384 A1 | 9/2009 | Aranyi |
| 2009/0277944 A9 | 11/2009 | Dalessandro et al. |
| 2010/0016855 A1 | 1/2010 | Ramstein et al. |
| 2010/0016888 A1 | 1/2010 | Calabrese et al. |
| 2010/0042110 A1 | 2/2010 | Kelley et al. |
| 2010/0087840 A1 | 4/2010 | Ebersole et al. |
| 2010/0147921 A1 | 6/2010 | Olson |
| 2010/0147922 A1 | 6/2010 | Olson |
| 2010/0174253 A1 | 7/2010 | Cline et al. |
| 2010/0203151 A1 | 8/2010 | Hiraoka |
| 2010/0243707 A1 | 9/2010 | Olson et al. |
| 2010/0331859 A1 | 12/2010 | Omori |
| 2011/0034910 A1 | 2/2011 | Ross et al. |
| 2011/0089220 A1 | 4/2011 | Ingmanson et al. |
| 2011/0125138 A1 | 5/2011 | Malinouskas et al. |
| 2011/0166673 A1 | 7/2011 | Patel et al. |
| 2011/0293690 A1 | 12/2011 | Griffin et al. |
| 2012/0080336 A1 | 4/2012 | Shelton, IV et al. |
| 2012/0145767 A1* | 6/2012 | Shah ............... A61B 17/07207 227/180.1 |
| 2012/0172891 A1 | 7/2012 | Lee |
| 2012/0197272 A1 | 8/2012 | Oray et al. |
| 2012/0241491 A1 | 9/2012 | Aldridge et al. |
| 2012/0241493 A1 | 9/2012 | Baxter, III et al. |
| 2012/0253298 A1 | 10/2012 | Henderson et al. |
| 2012/0273548 A1 | 11/2012 | Ma et al. |
| 2013/0153636 A1 | 6/2013 | Shelton, IV et al. |
| 2013/0153641 A1 | 6/2013 | Shelton, IV et al. |
| 2013/0209659 A1 | 8/2013 | Racenet et al. |
| 2013/0256380 A1 | 10/2013 | Schmid et al. |
| 2014/0048580 A1 | 2/2014 | Merchant et al. |
| 2014/0131418 A1 | 5/2014 | Kostrzewski |
| 2014/0239047 A1 | 8/2014 | Hodgkinson et al. |
| 2014/0288386 A1 | 9/2014 | Zand et al. |
| 2014/0343416 A1 | 11/2014 | Panescu et al. |
| 2015/0041347 A1 | 2/2015 | Hodgkinson |
| 2015/0133995 A1 | 5/2015 | Shelton, IV et al. |
| 2015/0209045 A1 | 7/2015 | Hodgkinson et al. |
| 2015/0297199 A1 | 10/2015 | Nicholas et al. |
| 2015/0327864 A1 | 11/2015 | Hodgkinson et al. |
| 2016/0022268 A1 | 1/2016 | Prior |
| 2016/0045200 A1 | 2/2016 | Milliman |
| 2016/0100834 A1 | 4/2016 | Viola et al. |
| 2016/0106430 A1 | 4/2016 | Carter et al. |
| 2016/0157857 A1 | 6/2016 | Hodgkinson et al. |
| 2016/0174988 A1 | 6/2016 | D'Agostino et al. |
| 2016/0206315 A1 | 7/2016 | Olson |
| 2016/0213288 A1* | 7/2016 | Wisniewski ......... A61B 5/7278 |
| 2016/0220257 A1 | 8/2016 | Casasanta et al. |
| 2016/0249923 A1 | 9/2016 | Hodgkinson et al. |
| 2016/0256166 A1 | 9/2016 | (Prommersberger) Stopek et al. |
| 2016/0270793 A1 | 9/2016 | Carter et al. |
| 2016/0310143 A1 | 10/2016 | Bettuchi |
| 2016/0338704 A1 | 11/2016 | Penna |
| 2016/0367252 A1 | 12/2016 | Olson et al. |
| 2016/0367253 A1 | 12/2016 | Hodgkinson |
| 2016/0367257 A1 | 12/2016 | Stevenson et al. |
| 2017/0042540 A1 | 2/2017 | Olson et al. |
| 2017/0049452 A1 | 2/2017 | Milliman |
| 2017/0150967 A1 | 6/2017 | Hodgkinson et al. |
| 2017/0172575 A1 | 6/2017 | Hodgkinson |
| 2017/0231629 A1 | 8/2017 | Stopek et al. |
| 2017/0238931 A1 | 8/2017 | Prescott et al. |
| 2017/0281328 A1 | 10/2017 | Hodgkinson et al. |
| 2017/0296188 A1 | 10/2017 | Ingmanson et al. |
| 2017/0354415 A1 | 12/2017 | Casasanta, Jr. et al. |

FOREIGN PATENT DOCUMENTS

| | | |
|---|---|---|
| DE | 1602563 U | 3/1950 |
| DE | 19924311 A1 | 11/2000 |
| EP | 0327022 A2 | 8/1989 |
| EP | 0594148 A1 | 4/1994 |
| EP | 2491867 A1 | 8/2012 |
| JP | 2000166933 A | 6/2000 |
| JP | 2002202213 A | 7/2002 |
| JP | 2007124166 A | 5/2007 |
| JP | 2010214132 A | 9/2010 |
| WO | 90/05489 A1 | 5/1990 |
| WO | 95/16221 A1 | 6/1995 |
| WO | 98/38923 A1 | 9/1998 |
| WO | 9926826 A2 | 6/1999 |
| WO | 0010456 A1 | 3/2000 |
| WO | 0016684 A1 | 3/2000 |
| WO | 2010/075298 A2 | 7/2010 |
| WO | 2014145020 A1 | 9/2014 |

OTHER PUBLICATIONS

Australian Examination Report No. 1 corresponding to AU 2014200793 dated Sep. 2, 2017.
Extended European Search Report corresponding to EP 17 17 8528.0 dated Oct. 13, 2017.
Australian Examination Report No. 1 corresponding to AU 2013234420 dated Oct. 24, 2017.
Japanese Office Action corresponding to JP 2013-175379 dated Oct. 20, 2017.
Japanese Office Action corresponding to JP 2013-147701 dated Oct. 27, 2017.
Extended European Search Report corresponding to EP 17 17 5656.2 dated Nov. 7, 2017.
Japanese Office Action corresponding to JP 2014-009738 dated Nov. 14, 2017.
European Office Action corresponding to EP 13 17 3986.4 dated Nov. 29, 2017.
Japanese Office Action corresponding to JP 2017-075975 dated Dec. 4, 2017.
European Office Action corresponding to EP 13 19 7958.5 dated Dec. 11, 2017.
Extended European Search Report corresponding to EP 14 16 9739.1, completed Aug. 19, 2014 and dated Aug. 29, 2014; (7 pp).
Extended European Search Report corresponding to EP 14 15 7997.9, completed Sep. 9, 2014 and dated Sep. 17, 2014; (8 pp).
Extended European Search Report corresponding to EP 14 16 8904.2, completed Sep. 10, 2014 and dated Sep. 18, 2014; (8 pp).
Extended European Search Report corresponding to EP 13 19 4995.0, completed Jun. 5, 2014 and dated Oct. 13, 2014; (10 pp).

(56) References Cited

OTHER PUBLICATIONS

Extended European Search Report corresponding to EP 13 15 4571.7, completed Oct. 10, 2014 and dated Oct. 20, 2014; (8 pp).
Extended European Search Report corresponding to EP 14 18 1125.7, completed Oct. 16, 2014 and dated Oct. 24, 2014; (7 pp).
Extended European Search Report corresponding to EP 14 18 1127.3, completed Oct. 16, 2014 and dated Nov. 10, 2014; (8 pp).
Extended European Search Report corresponding to EP 14 19 0419.3, completed Mar. 24, 2015 and dated Mar. 30, 2015; (6 pp).
Office Action corresponding to EP 12 198 776.2 dated Apr. 7, 2015.
European Office Action corresponding to EP 13 156 297.7 dated Apr. 10, 2015.
Australian Examination Report No. 1 corresponding to AU 2011250822 dated May 18, 2015.
European Office Action corresponding to EP 12 186 175.1 dated Jun. 1, 2015.
Chinese Office Action corresponding to CN 201010517292.8 dated Jun. 2, 2015.
Extended European Search Report corresponding to EP 14 17 4814.5 dated Jun. 9, 2015.
Australian Examination Report No. 1 corresponding to AU 2014200584 dated Jun. 15, 2015.
European Office Action corresponding to EP 13 180 881.8 dated Jun. 19, 2015.
European Office Action corresponding to EP 14 157 195.0 dated Jul. 2, 2015.
Extended European Search Report corresponding to EP 12 19 6902.6 dated Aug. 6, 2015.
Extended European Search Report corresponding to EP 14 15 2060.1 dated Aug. 14, 2015.
Chinese Office Action corresponding to CN 201210129787.2 dated Aug. 24, 2015.
Canadian Office Action corresponding to CA 2,665,206 dated Nov. 19, 2013.
Chinese Notification of Reexamination corresponding to CN 201010517292.8 dated Jun. 2, 2015.
Japanese Office Action corresponding to JP 2014-216989 dated Sep. 11, 2015.
Canadian First Office Action corresponding to CA 2,686,105 dated Sep. 17, 2015.
Japanese Office Action corresponding to JP 2012-040188 dated Oct. 21, 2015.
European Communication corresponding to EP 13 17 6895.4 dated Nov. 5, 2015.
Chinese First Office Action corresponding to CN 201210544552 dated Nov. 23, 2015.
Chinese First Office Action corresponding to CN 201210545228 dated Nov. 30, 2015.
Extended European Search Report corresponding to EP 15 18 0491.1 dated Dec. 9, 2015.
Extended European Search Report corresponding to EP 15 18 3819.0 dated Dec. 11, 2015.
Canadian Office Action corresponding to CA 2,697,819 dated Jan. 6, 2016.
Canadian Office Action corresponding to CA 2,696,419 dated Jan. 14, 2016.
European Office Action corresponding to EP 12 19 8776.2 dated Jan. 19, 2016.
Extended European Search Report corresponding to EP 15 17 4146.9 dated Jan. 20, 2016.
Chinese First Office Action corresponding to CN 201310353628.5 dated Jan. 25, 2016.
Extended European Search Report corresponding to EP 12 19 6912.5 dated Feb. 1, 2016.
Japanese Office Action corresponding to JP 2012-098903 dated Feb. 22, 2016.
Extended European Search Report corresponding to EP 12 19 8753.1 dated Feb. 24, 2016.
Chinese First Office Action corresponding to CN 201410449019.4 dated Mar. 30, 2016.
Extended European Search Report corresponding to EP 16 15 0232.3 dated Apr. 12, 2016.
European Office Action corresponding to EP 11 18 3256.4 dated Apr. 20, 2016.
Australian Examination Report No. 1 corresponding to AU 2012244169 dated May 10, 2016.
European Office Action corresponding to EP 10 25 0715.9 dated May 12, 2016.
Chinese First Office Action corresponding to CN 201410778512.0 dated May 13, 2016.
Australian Examination Report No. 1 corresponding to AU 2012227358 dated May 16, 2016.
Japanese Office Action corresponding to JP 2012-040188 dated May 17, 2016.
Australian Examination Report No. 1 corresponding to AU 2012244380 dated May 20, 2016.
Australian Examination Report No. 1 corresponding to AU 2014227480 dated May 21, 2016.
Australian Examination Report No. 1 corresponding to AU 2012254977 dated May 30, 2016.
European Search Report corresponding to EP 06 00 4598, completed Jun. 22, 2006; (2 pp).
European Search Report corresponding to EP 06 01 6962.0, completed Jan. 3, 2007 and dated Jan. 11, 2007; (10 pp).
International Search Report corresponding to International Application No. PCT/US2005/036740, completed Feb. 20, 2007 and dated Mar. 23, 2007; (8 pp).
International Search Report corresponding to International Application No. PCT/US2007/022713, completed Apr. 21, 2008 and dated May 15, 2008; (1 p).
International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).

(56) References Cited

OTHER PUBLICATIONS

Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresoinding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Extended European Search Report corresponding to EP 13 19 4995.0, completed Jun. 5, 2014 and dated Jun. 16, 2014; (5 pp).
Extended European Search Report corresponding to EP 14 15 7195.0, completed Jun. 5, 2014 and dated Jun. 18, 2014; (9 pp).
Extended European Search Report corresponding to EP 14 15 6342.9, completed Jul. 22, 2014 and dated Jul. 29, 2014; (8 pp).
European Office Action corresponding to EP 14 17 2681.0 dated May 13, 2016.
Extended European Search Report corresponding to EP 16 15 3647.9 dated Jun. 3, 2016.
Chinese Office Action corresponding to CN 201210545228 dated Jun. 29, 2016.
Japanese Office Action corresponding to JP 2012-250058 dated Jun. 29, 2016.
European Office Action corresponding to EP 14 15 7997.9 dated Jun. 29, 2016.
Canadian Office Action corresponding to CA 2,712,617 dated Jun. 30, 2016.
Chinese First Office Action corresponding to CN 2013103036903 dated Jun. 30, 2016.
Australian Patent Examination Report No. 1 corresponding to AU 2012250278 dated Jul. 10, 2016.
Australian Patent Examination Report No. 1 corresponding to AU 2012244382 dated Jul. 10, 2016.
Japanese Office Action corresponding to 2012-255242 dated Jul. 26, 2016.
Japanese Office Action corresponding to JP 2012-268668 dated Jul. 27, 2016
European Office Action corresponding to EP 14 15 2060.1 dated Aug. 4, 2016.
European Office Action corresponding to EP 12 16 5609.4 dated Aug. 5, 2016.
European Office Action corresponding to EP 15 15 2392.5 dated Aug. 8, 2016.
Japanese Office Action corresponding to JP 2013-003624 dated Aug. 25, 2016.
Australian Patent Examination Report No. 1 corresponding to AU 2012261752 dated Sep. 6, 2016.
Japanese Office Action corresponding to JP 2014-252703 dated Sep. 26, 2016.
European Office Action corresponding to EP 12 19 8776.2 dated Sep. 12, 2016.
Japanese Office Action corresponding to JP 2013-000321 dated Sep. 13, 2016.
Chinese Second Office Action corresponding to CN 201310353628.5 dated Sep. 26, 2016.
European Office Action corresponding to EP 12 15 2541.4 dated Sep. 27, 2016.
Australian Patent Examination Report No. 1 corresponding to AU 2012268923 dated Sep. 28, 2016.
Chinese First Office Action corresponding to CN 2013107068710 dated Dec. 16, 2016.
Chinese First Office Action corresponding to CN 201310646606.8 dated Dec. 23, 2016.
Japanese Office Action corresponding to JP 2013-000321 dated Jan. 4, 2017.
Extended European Search Report corresponding to EP 16 16 6367.9 dated Jan. 16, 2017.
Australian Examination Report No. 1 corresponding to AU 2013206777 dated Feb. 1, 2017.
Chinese Second Office Action corresponding to CN 2013103036903 dated Feb. 23, 2017.
Japanese Office Action corresponding to JP 2013-175379 dated Mar. 1, 2017.
Chinese First Office Action corresponding to CN 201410028462.4 dated Mar. 2, 2017.
Chinese First Office Action corresponding to CN 201410084070 dated Mar. 13, 2017.
Extended European Search Report corresponding to EP 16 19 6549.6 dated Mar. 17, 2017.
Japanese Office Action corresponding to JP 2013-147701 dated Mar. 21, 2017.
Australian Examination Report No. 1 corresponding to AU 2013206804 dated Mar. 21, 2017.
Australian Examination Report No. 1 corresponding to AU 2013211499 dated May 4, 2017.
Australian Examination Report No. 1 corresponding to AU 2014201008 dated May 23, 2017.
European Office Action corresponding to EP 15 17 4146.9 dated May 15, 2017.
Japanese Office Action corresponding to JP 2013-154561 dated May 23, 2017.
European Office Action corresponding to EP 12 19 4784.0 dated May 29, 2017.
Japanese Office Action corresponding to JP 2013-169083 dated May 31, 2017.
Australian Examination Report No. 1 corresponding to AU 2013213767 dated Jun. 29, 2017.
Australian Examination Report No. 2 corresponding to AU 2012261752 dated Jul. 7, 2017.
Australian Examination Report No. 1 corresponding to AU 2013266989 dated Jul. 10, 2017.
Extended European Search Report corresponding to EP 14 15 3609.4 dated Jul. 14, 2017.
Australian Examination Report No. 1 corresponding to AU 2013234418 dated Jul. 14, 2017.

(56) References Cited

OTHER PUBLICATIONS

Extended European Search Report corresponding to EP 14 15 3610.2 dated Jul. 17, 2017.
Australian Examination Report No. 1 corresponding to AU 2014200109 dated Jul. 20, 2017.
Australian Examination Report No. 1 corresponding to AU 2014200074 dated Jul. 20, 2017.
Japanese Office Action corresponding to JP 2013-250857 dated Aug. 17, 2017.
Japanese Office Action corresponding to JP 2013-229471 dated Aug. 17, 2017.

* cited by examiner

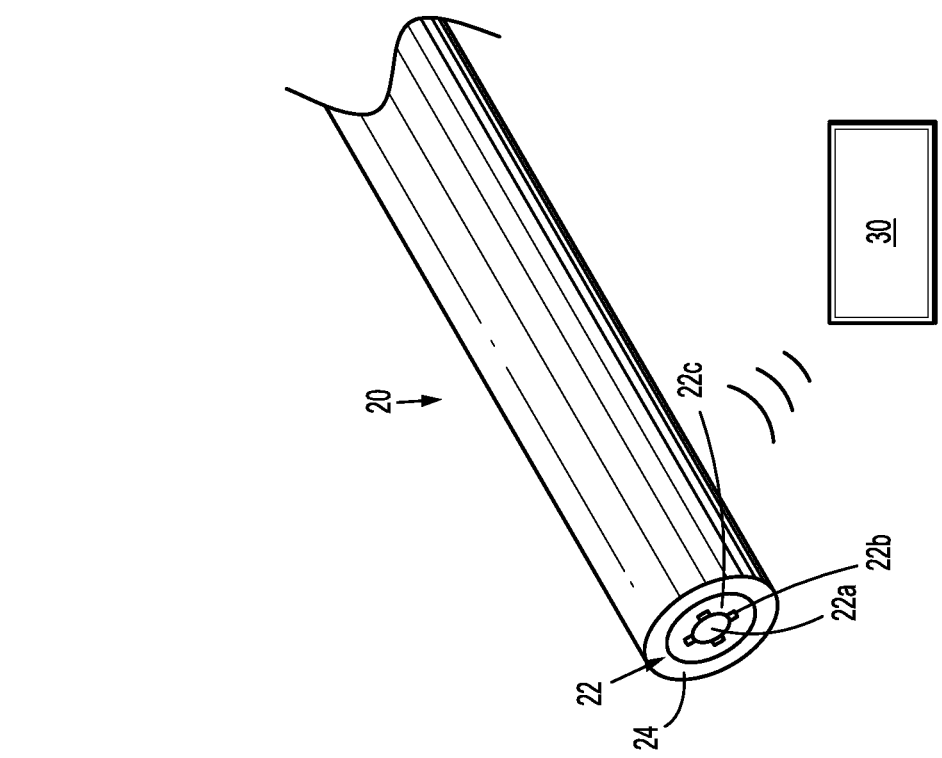
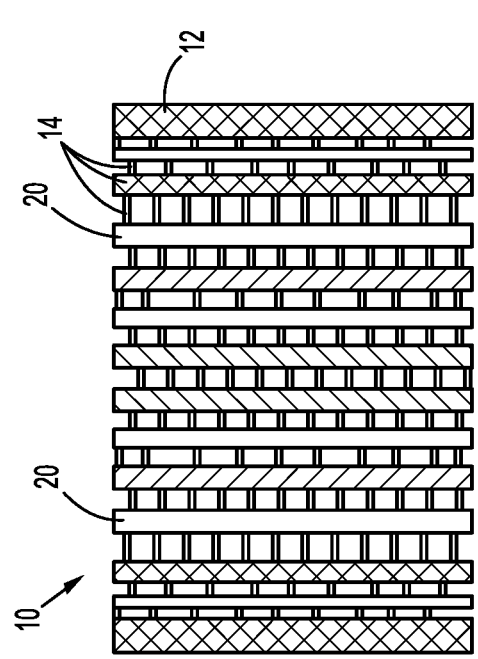
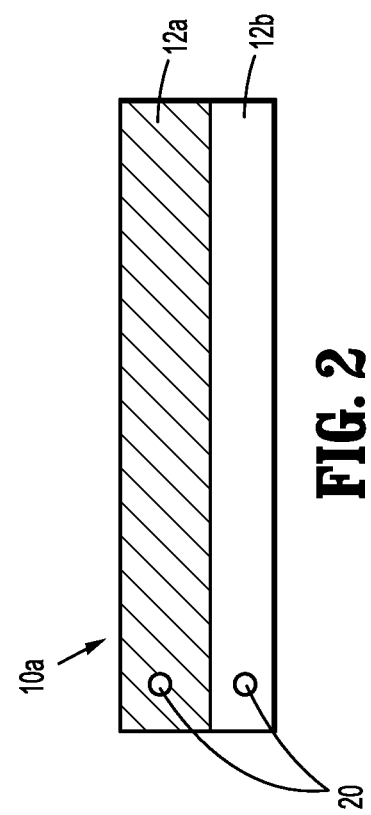
FIG. 1
FIG. 2
FIG. 3

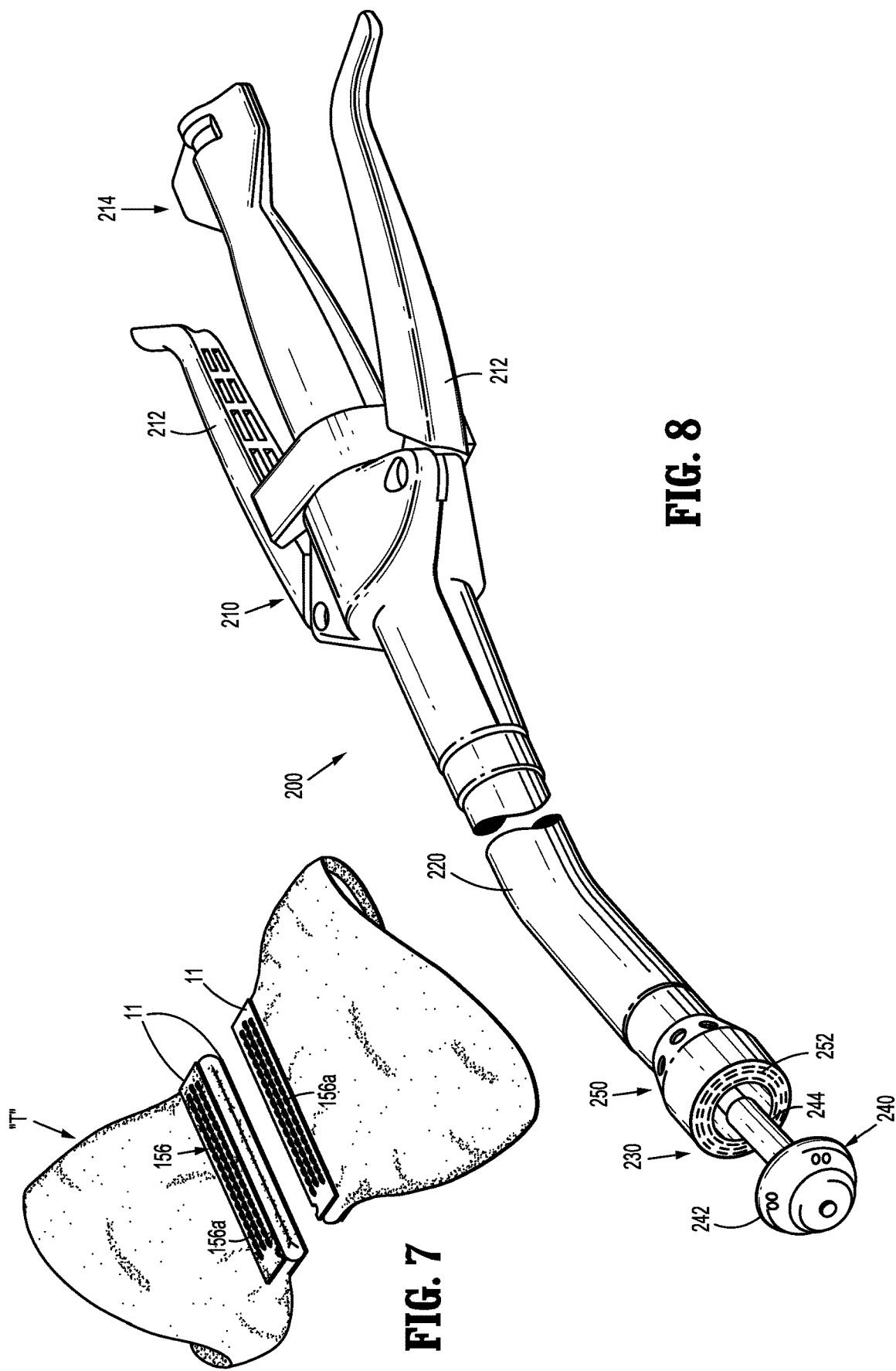

SURGICAL IMPLANTS INCLUDING SENSING FIBERS

CROSS-REFERENCE TO RELATED APPLICATIONS

This application claims the benefit of, and priority to, U.S. Provisional Patent Application Ser. No. 62/599,232, filed on Dec. 15, 2017 and U.S. Provisional Patent Application Ser. No. 62/477,458, filed on Mar. 28, 2017, the entire content of which is hereby incorporated by reference herein.

BACKGROUND

Technical Field

The present disclosure relates to surgical implants including sensing fibers for post-operative monitoring. Embodiments of the present disclosure relate to surgical buttresses that are releasably attached to a surgical stapling apparatus, and in particular, to a surgical buttress including sensing fibers for detecting tissue conditions along a staple line and transmitting the tissue conditions to a remote device. Embodiments of the present disclosure relate to a surgical mesh including sensing fibers for detecting tissue conditions at a soft tissue repair site and transmitting the tissue conditions to a remote device.

Background of Related Art

Surgical stapling apparatus are employed by surgeons to sequentially or simultaneously apply one or more rows of fasteners, e.g., staples or two-part fasteners, to body tissue for the purpose of joining segments of body tissue together and/or attaching a surgical implant to body tissue. Such apparatus generally include a pair of jaws or finger-like structures between which the body tissue to be joined is placed. When the stapling apparatus is actuated, or "fired", longitudinally moving firing bars contact staple drive members in one of the jaws. The staple drive members push the surgical staples through the body tissue and into an anvil in the opposite jaw which forms the staples. If tissue is to be removed or separated, a knife blade can be provided in the jaws of the apparatus to cut the tissue between the lines of staples.

Surgical supports, e.g., meshes or buttress materials, may be used in combination with surgical stapling apparatus to bridge, repair and/or reinforce tissue defects within a patient such as those occurring, for example, in the abdominal wall, chest wall, diaphragm, or musculo-aponeurotic areas of the body. A buttress material may reinforce a staple or suture line as well as cover the juncture of tissues to reduce leakage prior to healing. A mesh or patch may reinforce, replace, and/or augment soft tissue such as, the abdominal wall in the case of hernia repair.

For example, following surgery on the gastrointestinal system in which the bowel undergoes anastomosis, a possibility exists that an incidence may arise/develop of subsequent leakage from the bowel into the peritoneal cavity. The result of this development (e.g., impacts on morbidity and mortality) dramatically affects the patient's prognosis and largely impacts the cost of treatment. Leak detection is generally accomplished by monitoring clinical signs of infection, including white blood cell count, fever, malaise, heart rate, etc. A factor of using clinical signs is that there is a lag between the time the leak occurs and the onset of signs or symptoms. This may result in an escalation of the condition prior to its detection and the appropriate treatment being instituted.

Imaging modalities, such as fluoroscopy, may be utilized to monitor for leak detection after administering radiopaque dye orally or rectally. Imaging modalities, however, have limitations of sensitivity and specificity, and require significant resources and cost to perform. Additional leak detection attempts of measuring effluent from drains have demonstrated some success. Limitations of this approach, however, include the inconsistent use of drains due to concomitant effects (e.g., infection, clogging, migration, etc.) and identification of markers from drain fluid may be delayed significantly after the leak occurs.

As another example, post-surgical complications may arise after an abdominal wall hernia repair procedure. The performance of a hernia repair using a mesh fixed to an abdominal wall depends, in part, upon shear forces exerted upon the mesh and/or experienced at fixation points of the mesh to tissue due to, for example, changes in intra-abdominal pressure. Tearing, breakage, and/or bulging of the mesh may compromise the surgical repair of the hernia defect, or lead to mesh failure.

While devices and methods are available in attempts of identifying post-surgical complications, such as leaks and/or implant compromise, it would be advantageous to provide a real time non-invasive monitoring system for effective early detection of issues associated with a patient's health. Such a system would provide a clinician with a method of evaluating critical predictors of morbidity and mortality in patients in real time following surgery and/or tissue trauma. Acute stage detection would allow for early intervention resulting in improved patient outcomes. Additionally or alternatively, it would be advantageous to include a real time monitoring system as part of a post-operative regimen for improving patient recovery following surgical trauma and/or stress.

SUMMARY

A monitoring system in accordance with aspects of the present disclosure includes a surgical implant configured for implantation in vivo and having at least one sensing fiber configured to measure a preselected physiological parameter, and a receiving unit in wireless communication with the at least one sensing fiber and configured to receive measurements of the preselected physiological parameter.

The surgical implant may include a porous layer, and the at least one sensing fiber may be disposed within the porous layer. The surgical implant may be formed from a plurality of fibers, and the at least one sensing fiber may be incorporated into the plurality of fibers. The surgical implant may include a non-porous layer, and the at least one sensing fiber may be disposed within the non-porous layer.

In some aspects, the at least one sensing fiber is an optical fiber. In certain aspects, the preselected physiological parameter measured by the at least one sensing fiber is pH, in some other aspects, the preselected physiological parameter measured by the at least one sensing fiber is a quantity of an analyte, and in yet other aspects, the preselected physiological parameter measured by the at least one sensing fiber is force.

The at least one sensing fiber may include a core and a sheath disposed over the core. The core may include a semiconducting element, a conducting element, and an insulating element. In some aspects, the core includes a semiconducting element and a plurality of conducting elements in contact with the semiconducting element. In certain aspects, the plurality of conducting elements is electrically connected in a circuit.

A surgical system in accordance with aspects of the present disclosure includes an end effector having a plurality of fasteners and a surgical implant securable to tissue via the plurality of fasteners. The surgical implant includes at least one sensing fiber configured to measure a preselected physiological parameter.

In some aspects, the at least one sensing fiber is an optical sensor. The at least one sensing fiber may include a core and a sheath disposed over the core. The core may include a semiconducting element, a conducting element, and an insulating element. In some aspects, the core includes a semiconducting element and a plurality of conducting elements in contact with the semiconducting element. In certain aspects, the plurality of conducting elements is electrically connected in a circuit.

The surgical implant may be a surgical buttress releasably attached to the end effector. The surgical implant may be a surgical mesh including a plurality of fibers.

A surgical stapling apparatus in accordance with aspects of the present disclosure includes an end effector having a staple cartridge assembly and an anvil assembly, and a surgical buttress releasably attached to the staple cartridge assembly or the anvil assembly. The surgical buttress includes at least one sensing fiber configured to measure a preselected physiological parameter.

The surgical buttress may include a porous layer in which the at least one sensing fiber is disposed and/or a non-porous layer in which the at least one sensing fiber is disposed. In some aspects, the at least one sensing fiber is an optical sensor. In certain aspects, the preselected physiological parameter measured by the at least one sensing fiber is pH.

The at least one sensing fiber of the surgical buttress may include a core and a sheath disposed over the core. The core may include a semiconducting element, a conducting element, and an insulating element. In some aspects, the core includes a semiconducting element and a plurality of conducting elements in contact with the semiconducting element. In certain aspects, the plurality of conducting elements is electrically connected in a circuit.

A monitoring system in accordance with aspects of the present disclosure includes a surgical buttress and a receiving unit. The surgical buttress is configured for implantation in vivo and includes at least one sensing fiber configured to measure a preselected physiological parameter. The receiving unit is in wireless communication with the at least one sensing fiber and configured to receive measurements of the preselected physiological parameter.

The surgical buttress may include a porous layer in which the at least one sensing fiber is disposed and/or a non-porous layer in which the at least one sensing fiber is disposed. In some aspects, the at least one sensing fiber is an optical sensor. In certain aspects, the preselected physiological parameter measured by the at least one sensing fiber is pH.

The at least one sensing fiber of the surgical buttress may include a core and a sheath disposed over the core. The core may include a semiconducting element, a conducting element, and an insulating element. In some aspects, the core includes a semiconducting element and a plurality of conducting elements in contact with the semiconducting element. In certain aspects, the plurality of conducting elements is electrically connected in a circuit.

A method of in vivo monitoring of an anastomosis in real time includes: securing a surgical buttress to tissue, the surgical buttress including at least one sensing fiber configured to measure a preselected physiological parameter; and monitoring the preselected physiological parameter via data wirelessly received by a receiving unit from the at least one sensing fiber of the surgical buttress. In aspects, the method further includes: positioning a body portion of a surgical stapling device including a staple cartridge assembly adjacent a first tissue and positioning an anvil assembly of the surgical stapling device adjacent a second tissue, the staple cartridge assembly or the anvil assembly including the surgical buttress releasably retained thereon; and firing the surgical stapling device to mechanically secure the surgical buttress and the first and second tissues with staples from the staple cartridge assembly along a staple line.

Other aspects, features, and advantages will be apparent from the description, drawings, and the claims.

BRIEF DESCRIPTION OF THE DRAWINGS

Various aspects of the present disclosure are described herein below with reference to the drawings, which are incorporated in and constitute a part of this specification, wherein:

FIG. 1 is a top view of a surgical implant in accordance with an embodiment of the present disclosure;

FIG. 2 is a side view of a surgical implant in accordance with another embodiment of the present disclosure;

FIG. 3 is a schematic illustration of a monitoring system including a sensing fiber of the surgical implant of FIG. 1 or FIG. 2, and a receiving unit in accordance with an embodiment of the present disclosure;

FIG. 7 is a perspective view of the stapled and divided tissue of FIG. 6;

FIG. 8 is a perspective view of a surgical stapling apparatus in accordance with another embodiment of the present disclosure;

DETAILED DESCRIPTION OF THE EMBODIMENTS

Figure 4:
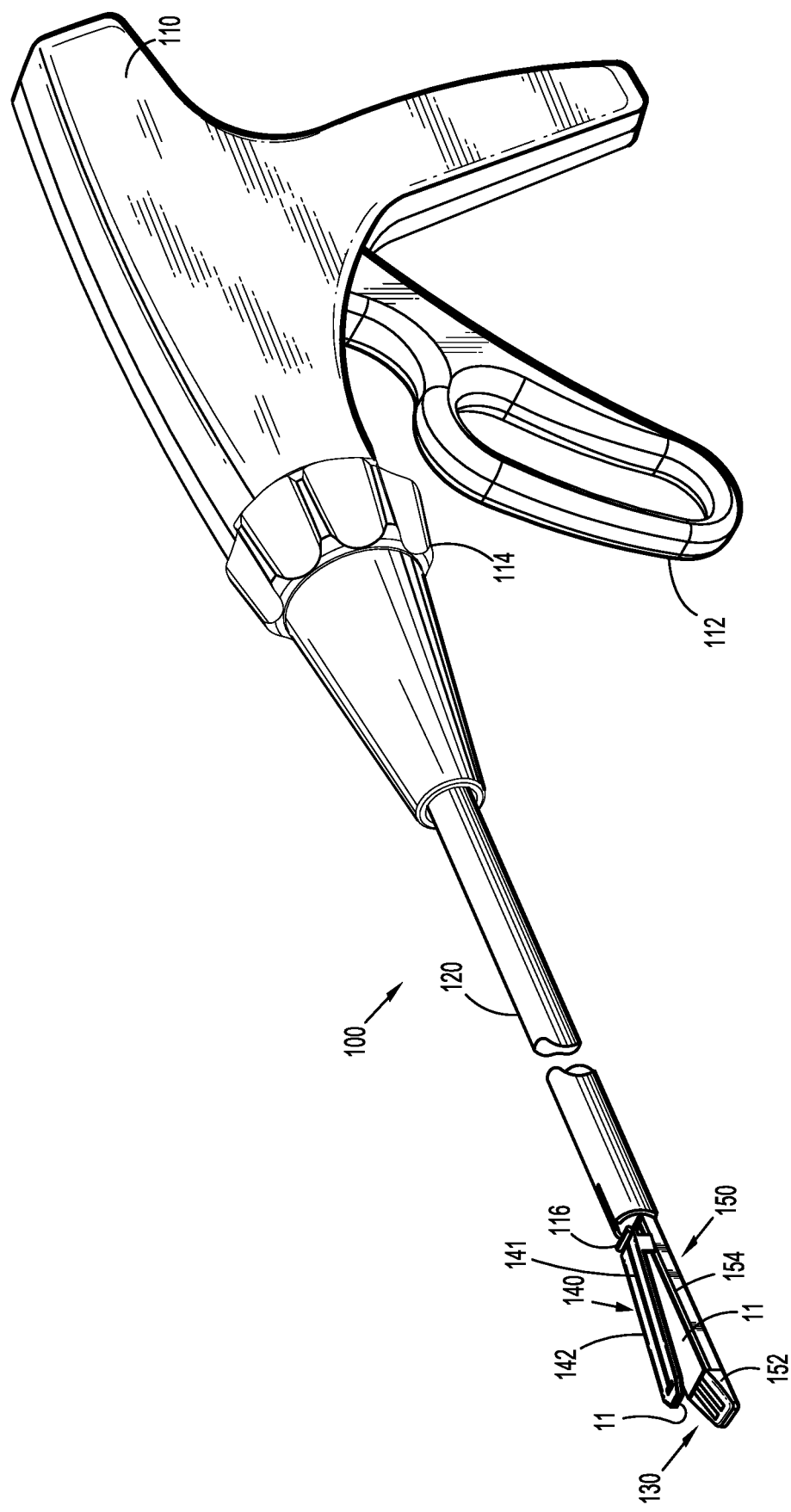
FIG. 4 is a perspective view of a surgical stapling apparatus including a surgical buttress disposed on an anvil assembly of the surgical stapling apparatus and a surgical buttress disposed on a staple cartridge assembly of the surgical stapling apparatus in accordance with an embodiment of the present disclosure.

The present disclosure is directed to surgical implants, systems, and methods of using the same for measuring physiological parameters in real time. The physiological parameters may be associated with acute and/or chronic tissue compromise or failure in one or multiple tissue/organ sites. The present disclosure describes embodiments of surgical implants for real time monitoring of physiological parameters, surgical stapling apparatus supporting and/or securing said surgical implants to tissue, monitoring systems including said surgical implants and a receiving unit for analysis of the physiological parameters, and exemplary corresponding methods of use in accordance with principles of the present disclosure.

The presently disclosed surgical implants may be any medical device, such as scaffolds, grafts, patches, slings, pledgets, growth matrices, drug delivery devices, wound plugs, and, in general, may be soft tissue repair devices and/or surgical prostheses. It should be understood that the surgical implants may also be utilized as topically applied medical products, such as wound dressings, coverings, and the like, that can be used in medical/surgical procedures. The principles of the present disclosure are related to monitoring of surgical and medical treatments of disease and body ailments of a patient, such as necrosis, infection, and cancer. For example, devices, systems, and methods of the present disclosure may be utilized in the detection of infection, metabolic disorder, or abnormal or non-ideal conditions of wound healing.

Embodiments of the presently disclosed surgical implants will now be described in detail with reference to the drawing figures wherein like reference numerals identify similar or identical elements. Throughout this description, the term "proximal" refers to a portion of a structure, or component thereof, that is closer to a clinician, and the term "distal" refers to a portion of the structure, or component thereof, that is farther from the clinician. As used herein, the term "patient" should be understood as referring to a human subject or other animal, and the term "clinician" should be understood as referring to a doctor, nurse, or other care provider and may include support personnel.

Referring now to FIG. 1, a surgical implant 10 in accordance with the present disclosure is shown. The surgical implant 10 may have any shape, size, and/or dimension suitable for its intended application as should be understood by those skilled in the art. The surgical implant 10 is fabricated from biocompatible materials which are bioabsorbable or non-absorbable, natural or synthetic materials. It should be understood that any combination of natural, synthetic, bioabsorbable, and/or non-bioabsorbable materials may be used to form the surgical implant 10.

The surgical implant 10 may be porous, non-porous, or combinations thereof. Suitable porous structures include, for example, fibrous structures (e.g., knitted structures, woven structures, and non-woven structures) and/or foams (e.g., open or closed cell foams). Suitable non-porous structures include, for example, films. The surgical implant 10 described herein may be a single porous or non-porous layer, or include a plurality of layers including any combination of porous and non-porous layers. For example, a surgical implant may include multiple porous and non-porous layers that are stacked in an alternating manner. In another example, a surgical implant may be formed in a "sandwich-like" manner wherein the outer layers of the surgical implant are porous and the inner layer(s) are non-porous.

Porous layer(s) in the surgical implant may enhance the ability of the surgical implant to absorb fluid, reduce bleeding, and seal the wound. Also, the porous layer(s) may allow for tissue ingrowth to fix the surgical implant in place. Non-porous layer(s) in the surgical implant may enhance the ability of the surgical implant to resist tears and perforations during the manufacturing, shipping, handling, and securing (e.g., stapling) processes. Also, non-porous layer(s) may retard or prevent tissue ingrowth from surrounding tissues thereby acting as an adhesion barrier and preventing the formation of unwanted scar tissue.

As shown in FIG. 1, the surgical implant 10 includes a single porous layer 12 having a fibrous structure. The porous layer 12 is formed from a plurality of interconnected fibers 14. The fibers 14 may be biocompatible polymeric and/or metallic materials in the form of filaments, threads, and/or yarns that are, for example, knitted or woven together, or may be staple fibers such as those used for preparing non-woven materials. Suitable techniques for assembling the fibers 14 are within the purview of those skilled in the art. The porous layer 12 of the surgical implant 10 further includes one or more sensing fibers 20 assembled with the fibers 14, or otherwise incorporated into the porous layer 12 of the surgical buttress 10, in a desired configuration based on, for example, in vivo sensing needs.

As discussed above, the surgical implant 10 may have other configurations. For example, as shown in FIG. 2, a surgical implant 10a includes a porous layer 12a and a non-porous layer 12b. Sensing fiber(s) 20 may be disposed in either or both the porous and non-porous layers 12a, 12b. It should be understood that at least one sensing fiber 20 is associated with a surgical implant 10, 10a and that the sensing fiber(s) may be disposed within a porous layer (e.g., fibrous structure or foam), a non-porous layer (e.g., a film), or combinations thereof depending on the configuration of the surgical implant 10, 10a.

Referring now to FIG. 3, the sensing fiber 20 is a sensor configured to measure a preselected physiological parameter of interest and to transmit signals relating to the physiological parameter to a receiving unit 30. The preselected physiological parameter may be a mechanical characteristic (e.g., relaxation, creep, etc.) of the tissue to which the surgical implant 10, 10a (FIGS. 1-2, respectively) is secured, or a substance (e.g., analytes, biomarkers, etc.) in the tissue and/or the tissue environment indicative of a physiological condition or state such as, for example, tissue perfusion, tissue ischemia, tissue reperfusion, infection, etc.

The sensing fiber 20 may be: an optical or electrical sensor for measuring characteristics such as impedance, temperature, pH, the presence and/or level of analytes, etc.; a mechanical sensor for measuring, for example, characteristics such as force, stress, strain, etc.; a conductivity or resistivity sensor for measuring, for example, ionic concentration of a compound; among other sensors within the purview of those skilled in the art for physical or chemical sensing. It should be understood that a surgical implant 10, 10a may include multiple sensing fibers 20 that measure the same or different characteristics.

With continued reference to FIG. 3, the sensing fiber 20 includes a core 22 configured to measure and transmit signals related to the preselected physiological parameter to the receiving unit 30, and a sheath 24 disposed over the core 22. While the sensing fiber 20 is shown having a circular cross-section, it should be understood that the sensing fiber 20 may have other cross-sectional shapes such as, for example, elliptical, triangular, and rectangular, among other regular and irregular shapes. Additionally, it should be understood that the core 22 may be off-center with respect to the sheath 24 or a plurality of cores 22 may be disposed within the sheath 24 such that the sensing fiber 20 exhibits an islands-in-the-sea arrangement where two or more "islands" (e.g., cores) are surrounded by a "sea" (e.g., sheath).

The core 22 includes one or more semiconducting elements 22a for measuring the physiological parameter, one or more conducting elements 22b (e.g., electrodes) connected in a circuit, and one or more insulating elements 22c disposed between and/or around the semiconducting and/or conducting elements 22a, 22b. The semiconducting element(s) 22a of the core 22 may be formed from a chalcogenide glass, the conducting element(s) 22b of the core 22 may be formed from a metal or metal alloy, and the insulating element(s) 22c of the core 22 and/or the sheath 24 may be formed, for example, from a thermoplastic polymer or copolymer such as polyetherether ketone, polyetherimide, polyether sulfone, polysulfone, polycarbonate, polyethylene, polymethyl methacrylate, or polytetrafluoroethylene.

The semiconducting, conducting, and insulating elements 22a, 22b, 22c are configured in a specific geometry (e.g., with selected material interfaces) during fabrication of the sensing fiber 20 to enable a desired sensing functionality. Accordingly, it should be understood that the core 22 of the sensing fiber 20 may have any of a variety of configurations (e.g., the core 22 can be solid or include spaces or gaps, may be symmetrical or non-symmetrical, etc.).

The sensing fiber 20 is wireless and may be powered externally via, e.g., radiofrequency or magnetic telemetry, to run continuously or be activated intermittently. The receiving unit 30 is an extracorporeal device configured to communicate with the sensing fiber 20 via a wireless (e.g., radiofrequency, optical, WiFi, Bluetooth®, LTE, etc.) connection to collect the signals from the sensing fiber 20 in real time and to process the signals into digital data. The receiving unit 30 may be a portable electronic device which may be worn by a patient (e.g., a wristwatch or transcorporeal patch), or otherwise carried by the patient (e.g., a mobile device such as a cell phone, or a unit disposed within a carrying case) to allow for patient mobility during post-surgical monitoring.

The signals/data collected by the receiving unit 30 may also be sent to a mobile device of a clinician or be transmitted to a cloud such that a clinician can access the information. The receiving unit 30 may provide a sensor alert via an indicator (e.g., a visual, audio, or other sensory indicator) to the patient and/or a clinician when a predetermined test criterion is met to allow for appropriate medical response based on the information received. The signals produced by the sensing fiber 20 contain information about a specific characteristic of the tissue and/or tissue environment which, in turn, imparts information about a condition or state of the tissue which can be utilized in determining a proper course of treatment.

With reference now to FIGS. 4-10, various exemplary embodiments of the surgical implants of the present disclosure are discussed in terms of surgical buttresses for use with surgical stapling apparatus. While these embodiments are directed to the detection of leaks of gastrointestinal content into the abdomen following anastomosis, it is envisioned that the principles of the present disclosure are equally applicable to a range of in vivo diagnostic applications, as discussed above.

The surgical buttresses may be used in sealing a wound by approximating the edges of wound tissue between a staple cartridge assembly and an anvil assembly of a surgical stapling apparatus which includes at least one surgical buttress having sensing fiber(s). The surgical buttress is releasably attached to the surgical stapling apparatus such that staples fired from the surgical stapling apparatus attach the surgical buttress to tissue. The sensing fibers of the surgical buttress measure a physiological parameter of the tissue and/or tissue environment and transmit the data to a receiving unit for monitoring by a clinician or the patient.

It should be understood that a variety of surgical stapling apparatus may be utilized with a surgical buttress of the present disclosure. For example, linear staplers may be utilized, such as, for example those including Duet TRS™ reloads and staplers with Tri-Staple™ technology, available through Medtronic, formerly Covidien (North Haven, Conn.), as well as other anastomosis staplers, such as, for example, EEA™, CEEA™, GIA™, EndoGIA™, and TA™, also available through Medtronic. It should also be appreciated that the principles of the present disclosure are equally applicable to surgical staplers having a variety of configurations, such as, for example, end-to-end anastomosis staplers having a circular cartridge and anvil (see, e.g., commonly owned U.S. Pat. No. 5,915,616, entitled "Surgical Fastener Applying Apparatus," the entire content of which is incorporated herein by this reference); laparoscopic staplers (see, e.g., commonly owned U.S. Pat. Nos. 6,330,965 and 6,241,139, each entitled "Surgical Stapling Apparatus," the entire contents of each of which being incorporated herein by this reference); and transverse anastomosis staplers (see, e.g., commonly owned U.S. Pat. Nos. 5,964,394 and 7,334,717, each entitled "Surgical Fastener Applying Apparatus", the entire contents of each of which being incorporated herein by this reference).

It is additionally appreciated that the principles of the present disclosure are equally applicable to powered hand-held electromechanical surgical staplers having a variety of configurations, such as, for example, those shown and described in U.S. Patent Application Publication No. 2015/0297199, the entire contents of each of which is incorporated herein by this reference).

Referring now to FIG. 4, an exemplary surgical stapling apparatus or surgical stapler 100 is shown for use in stapling tissue and applying a surgical implant in the form of a buttress material or surgical buttress 11 to the tissue. The surgical stapling apparatus 100 generally includes a handle assembly 110, an elongate tubular body portion 120 extending distally from the handle assembly 110, and an end effector or jaw assembly 130 extending distally from the elongate tubular body portion 120. The jaw assembly 130 includes an anvil assembly 140 including a staple clinching anvil jaw member 142 and a staple cartridge assembly 150 including a cartridge receiving jaw member 152 housing a staple cartridge 154. The jaw assembly 130 may be permanently affixed to the elongate tubular body portion 120 or may be detachable with respect to the elongate tubular body portion 120 and thus, replaceable with a new jaw assembly 130. Additionally or alternatively, the staple cartridge 154 may be removable and replaceable in the receiving jaw member 152 of the staple cartridge assembly 150. The anvil assembly 140 is pivotable with respect to the elongate tubular body portion 120 and is movable between an open position spaced apart from the staple cartridge assembly 150 and a closed position substantially adjacent the staple cartridge assembly 150. It is envisioned that, additionally or alternatively, the staple cartridge assembly 150 may be pivotable with respect to the elongate tubular body portion 120.

The surgical stapling apparatus 100 further includes a trigger 112 movably mounted on the handle assembly 110. Actuation of the trigger 112 initially operates to move the anvil assembly 140 from the open position to the closed position relative to staple cartridge assembly 150 and subsequently actuates the surgical stapling apparatus 100 to apply lines of staples to tissue captured between the anvil and staple cartridge assemblies 140, 150. Specifically, a driver 116 is provided to move the anvil jaw member 142 between the open and closed positions relative to the receiving jaw member 152. The driver 116 moves between a longitudinal slot 141 formed in the anvil jaw member 142, and a knife 118 (FIG. 6) associated with the driver 116 cuts tissue captured between the anvil and staple cartridge assemblies 140, 150 as the driver 116 passes through the longitudinal slot 141 of the anvil jaw member 142, as described in further detail below.

In order to properly orient the jaw assembly 130 relative to the tissue to be stapled, the surgical stapling apparatus 100 includes a rotation knob 114 mounted on the handle assembly 110. Rotation of the rotation knob 114 relative to the handle assembly 110 rotates the elongate tubular body portion 120 and the jaw assembly 130 relative to the handle assembly 110 so as to properly orient the jaw assembly 130 relative to the tissue to be stapled.

With continued reference to FIG. 4, respective surgical buttresses 11 are releasably attached to tissue facing surfaces (not explicitly shown) of the anvil assembly 140 and the staple cartridge assembly 150. The surgical buttress 11 may be releasably attached to the anvil assembly 140 and/or the staple cartridge assembly 150 via any suitable attachment feature within the purview of those skilled in the art, such as chemical attachment features (e.g., adhesives) and mechanical attachment features (e.g., mounting structures, such as pins or straps). The surgical buttress 11 is provided to reinforce and seal staple lines applied to tissue by the surgical stapling apparatus 100 and to measure a preselected physiological parameter of the tissue and/or the tissue environment.

It should be understood that while the surgical buttresses 11 are shown and described herein as being associated with both the anvil assembly 140 and the staple cartridge assembly 150, the surgical buttresses may be the same or different, or may only be associated with either the anvil assembly or the staple cartridge assembly, depending on, for example, the surgical application and/or desired placement and monitoring as should be understood by a person of ordinary skill in the art.

The surgical buttress 11 may have any shape, size, and/or dimension suitable to fit a surgical stapling apparatus. The surgical buttress is fabricated from biocompatible material(s) and may be porous, non-porous, or combinations thereof, as discussed above. The surgical buttress 10a includes at least one sensing fiber 20 (FIG. 3). In some embodiments, the surgical buttress 11 is configured the same as, or similar to, surgical implant 10 or 10a (FIGS. 1-2, respectively).

In embodiments, the sensing fiber 20 of the surgical buttress 11 is configured to measure a physiological parameter of interest related to monitoring for anastomosis leakage about a staple line. In some embodiments, the sensing fiber 20 is an optical pH sensor adapted to measure changes in pH in the tissue environment adjacent the staple line. In some embodiments, the sensing fiber 20 is a chemical sensor adapted to detect the presence of an analyte indicative of anastomotic leakage. The analyte to be detected can be an endogenous material that would normally only be present within a patient's body (e.g., intestines, etc.) such as E. coli or blood, or an exogenous material introduced into the patient's body and that remains within the body unless leakage occurs.

Figure 5:
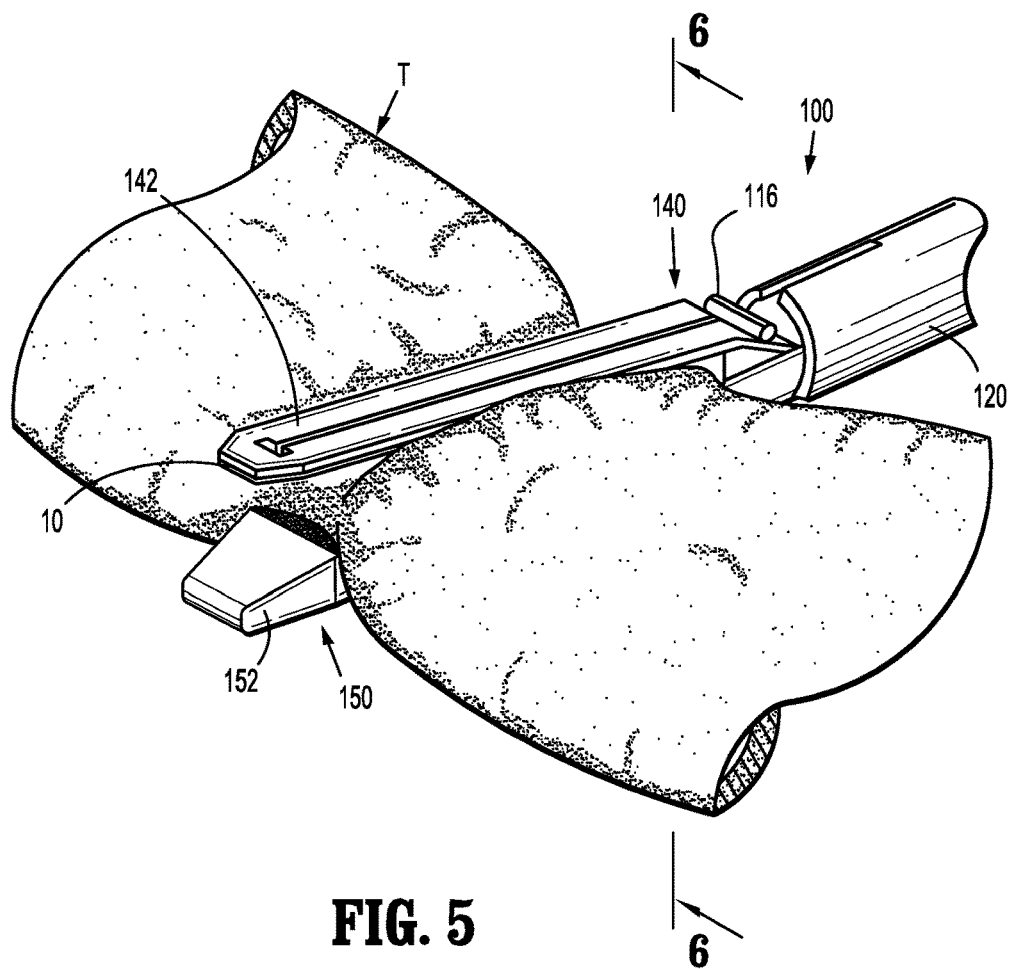
FIG. 5 is a perspective view of a distal end of the surgical stapling apparatus of FIG. 4, shown in use and positioned about tissue.

As shown in FIG. 5, during use of the surgical stapling apparatus 100, the anvil assembly 140 and the staple cartridge assembly 150, which have each been loaded with a surgical buttress 11, are positioned on opposed sides of a surgical site where adjacent first and second layers of tissue "T" are to be fastened to one another.

Figure 6:
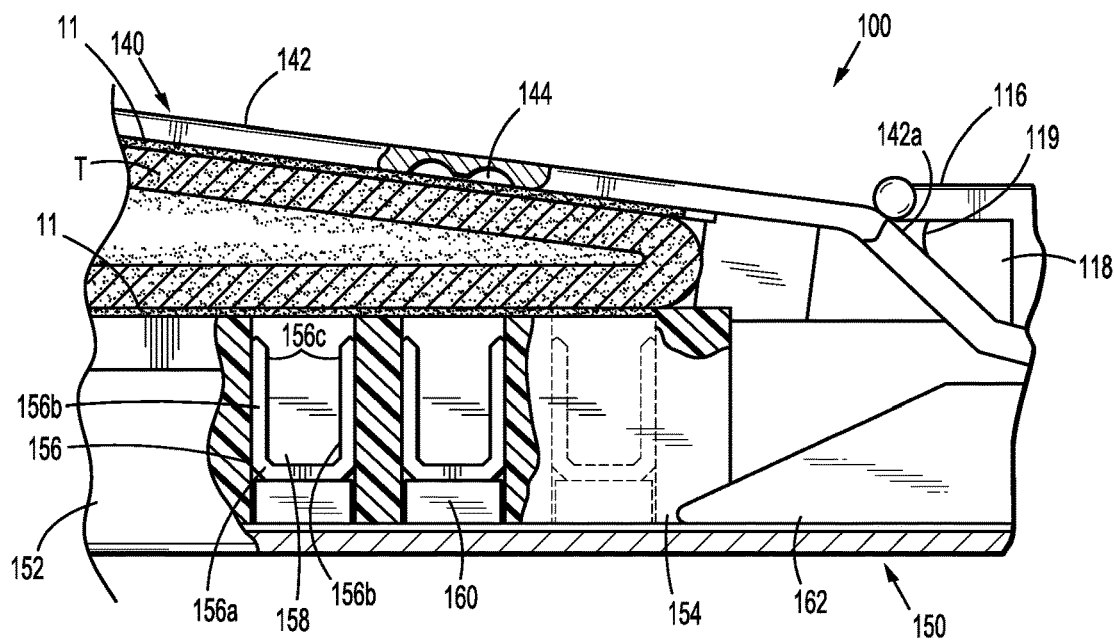
FIG. 6 is a cross-sectional view of the distal end of the surgical stapling apparatus of FIGS. 4 and 5, taken along line 6-6 of FIG. 5.

As shown in FIG. 6, the staple cartridge 154 includes surgical staples 156 positioned within individual staple pockets 158. The staples 156 are of a conventional type with each including a backspan 156a and a pair of legs 156b extending from the backspan 156a and terminating in tissue penetrating tips 156c. Staple pushers 160 are located within the staple pockets 158 and are positioned between the staples 156 and the path of a drive bar 162.

The surgical stapling apparatus 100 is initially actuated by movement of the trigger 112 (FIG. 4) relative to handle assembly 110 causing the driver 116 to move distally against a sloped edge 142a of the anvil jaw member 142 thereby causing the anvil jaw member 142 to be moved to the closed position relative to receiving jaw member 152 of the staple cartridge assembly 150. As the drive bar 162 advances distally within the staple cartridge 154, the drive bar 162 urges the staple pushers 160 upwardly against the backspan 156a of the staples 156 driving the legs 156b of the staples 156 through the surgical buttress 11 associated with the staple cartridge assembly 150, the tissue "T", the surgical buttress 11 associated with the anvil assembly 140, and towards staple forming pockets 144 defined in the anvil jaw member 142. The tissue penetrating tips 156c of the legs 156b of the staples 156 are bent within the staple forming pockets 144 of the anvil jaw member 142 such that the backspan 156a and the legs 156b secure the surgical buttresses 11 against the tissue "T".

Upon full actuation of surgical stapling apparatus 100, a knife 118 defining a knife blade 119, which is carried by the driver 116, cuts the tissue "T" between the rows of now formed staples 156. Upon movement of the anvil assembly 140 to the open position spaced apart from the staple cartridge assembly 150, the surgical buttresses 11 are pulled away from the anvil and staple cartridge assemblies 140, 150.

The resulting tissue "T", divided and stapled closed with the staples 156, is illustrated in FIG. 7. Specifically, the surgical buttress 11 that was associated with the staple cartridge assembly 150 is secured against the tissue "T" by the backspans 156a of the staples 156 and the surgical buttress 11 associated with the anvil assembly 140 is secured against the tissue "T" by the legs 156b of the staples 156. Thus, the surgical buttresses 11 are stapled to the tissue "T" thereby sealing and reinforcing the staple lines created by the staples 156, as well as allowing a clinician to monitor properties on each side of, and through, the stapled tissue "T" via the sensing fiber(s) 20 (FIG. 3) of the surgical buttresses 11. As discussed above, the sensing fibers 20 transmit information to the clinician such that if a specified test criterion is met, a course of treatment may be selected, e.g., antibiotic therapy, surgical intervention, etc. On the other hand, if no indicator of an abnormal physiological condition or state is provided, no further action is required on the part of the clinician.

Figure 9:
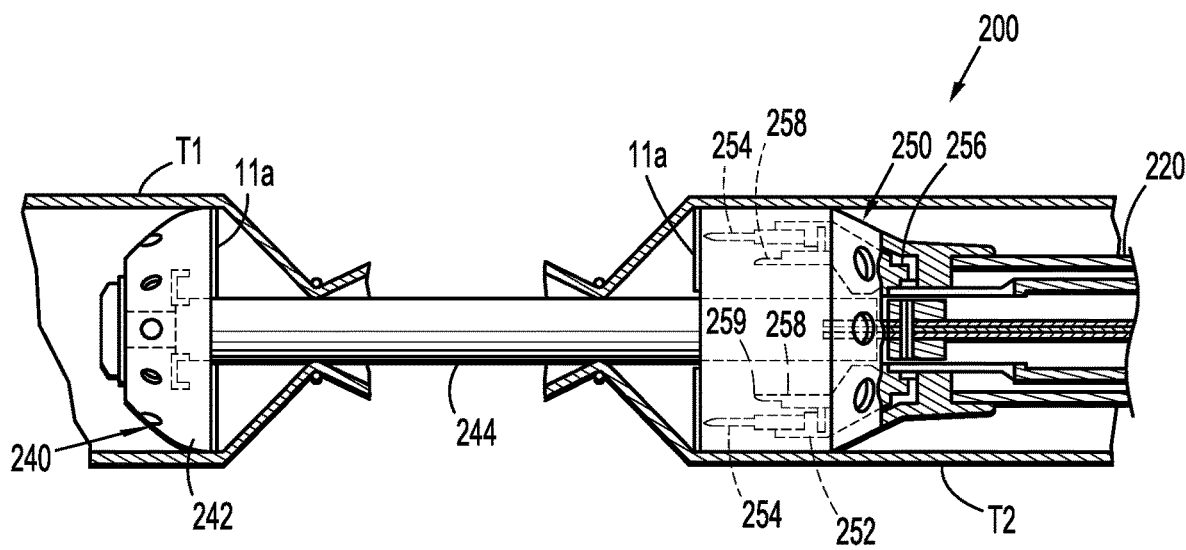
FIG. 9 is a cross-sectional view of the surgical stapling apparatus of FIG. 8 including a surgical buttress disposed on an anvil assembly of the surgical stapling apparatus and a surgical buttress disposed on a staple cartridge assembly of the surgical stapling apparatus in accordance with an embodiment of the present disclosure.
Figure 10:
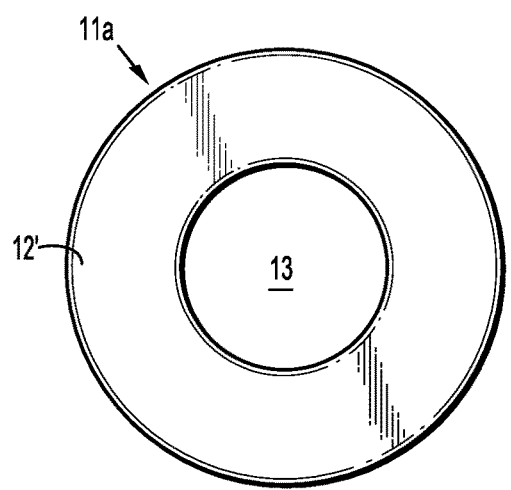
FIG. 10 is a top view of one of the surgical buttresses of FIG. 9.

Referring now to FIGS. 8 and 9, an annular surgical stapling apparatus 200, for use with a surgical buttress of the present disclosure, is shown. The surgical stapling apparatus 200 includes a handle assembly 210, an elongate tubular body portion 220 extending distally from the handle assembly 210, and an end effector 230 disposed at a distal end of the elongate tubular body portion 220. The handle assembly 210 has at least one pivotable actuating handle member 212, and an advancing member 214. The elongate tubular body portion 220 terminates in a staple cartridge assembly 250 of the end effector 230 which includes a pair of annular arrays of staple receiving slots 252 having a staple 254 disposed in each one of the staple receiving slots 252. Positioned distally of the staple cartridge assembly 250 is an anvil assembly 240 of the end effector 230 which includes an anvil member 242 and a shaft 244 operatively associated therewith for removably connecting the anvil assembly 240 to a distal end portion of the elongate tubular body portion 220 of the surgical stapling apparatus 200.

The staple cartridge assembly 250 may be fixedly connected to the distal end of the elongate tubular body portion 220 or may be configured to concentrically fit within the distal end of the elongate tubular body portion 220. The staple cartridge assembly 250 includes a staple pusher 256 including a proximal portion having a generally frustoconical shape and a distal portion defining two concentric rings of peripherally spaced fingers (not shown), each one of which is received within a respective staple receiving slot 252.

A knife 258, substantially in the form of an open cup with the rim thereof defining a knife blade 259, is disposed within the staple cartridge assembly 250 and mounted to a distal surface of the staple pusher 256. The knife 258 is disposed radially inward of the pair of annular arrays of staples 254. Accordingly, in use, as the staple pusher 256 is advanced, the knife 258 is also advanced axially outward.

A surgical buttress 11a is releasably attached to the anvil assembly 240 and/or the staple cartridge assembly 250. As specifically shown in FIG. 10, the surgical buttress 11a is provided in an annular configuration and includes a body portion 12' defining an aperture 13 that is sized and dimensioned to receive the shaft 244 (FIG. 9) of the anvil assembly 240 and allow free passage of the knife 258 (FIG. 9) therethrough. The body portion 12' of the surgical buttress 11a may be configured as one or more porous and/or non-porous layers as described above with regard to surgical buttress 11, and which includes at least one sensing fiber 20 (FIG. 3) disposed therein, as also described above.

Referring again to FIG. 9, the surgical stapling apparatus 200 and detachable anvil assembly 240 are used in an anastomosis procedure to effect joining of intestinal sections. The anastomosis procedure is typically performed using minimally invasive surgical techniques including laparoscopic means and instrumentation. The anvil assembly 240 is applied to an operative site either through a surgical incision or transanally and positioned within a first intestinal tissue section "T1", and the elongate tubular body portion 220 of the surgical stapling apparatus 200 is inserted through a surgical incision or transanally into a second intestinal tissue section "T2".

Thereafter, a clinician maneuvers the anvil assembly 240 until the proximal end of shaft 244 is inserted into the distal end of the tubular body portion 220 of the surgical stapling apparatus 200, wherein a mounting structure (not shown) within the distal end of tubular body portion 220 engages the shaft 244 of the anvil assembly 240 to effect mounting. The anvil assembly 240 and the tubular body portion 220 are then approximated to approximate the first and second tissue sections "T1", "T2". The surgical stapling apparatus 200 is then fired, firing the staples 254 through the surgical buttresses 11a as well as the first and second tissue sections "T1", "T2", effecting stapling of the first and second tissue sections "T1", "T2" to one another and cutting of the first and second tissue sections "T1", "T2" by the knife 258 to complete the anastomosis. Upon movement of the anvil assembly 240 away from the staple cartridge assembly 250, the surgical buttresses 11a are pulled away from the anvil and staple cartridge assemblies 240, 250.

As described above, the surgical buttresses 11a are stapled to the first and second tissue sections "T1", "T2" thereby sealing and reinforcing the staple lines created by the staples 254, as well as allowing a clinician to monitor properties on each side of, and through, the stapled first and second tissue sections "T1", "T2" via the sensing fiber(s) 20 (FIG. 3).

Figure 11:
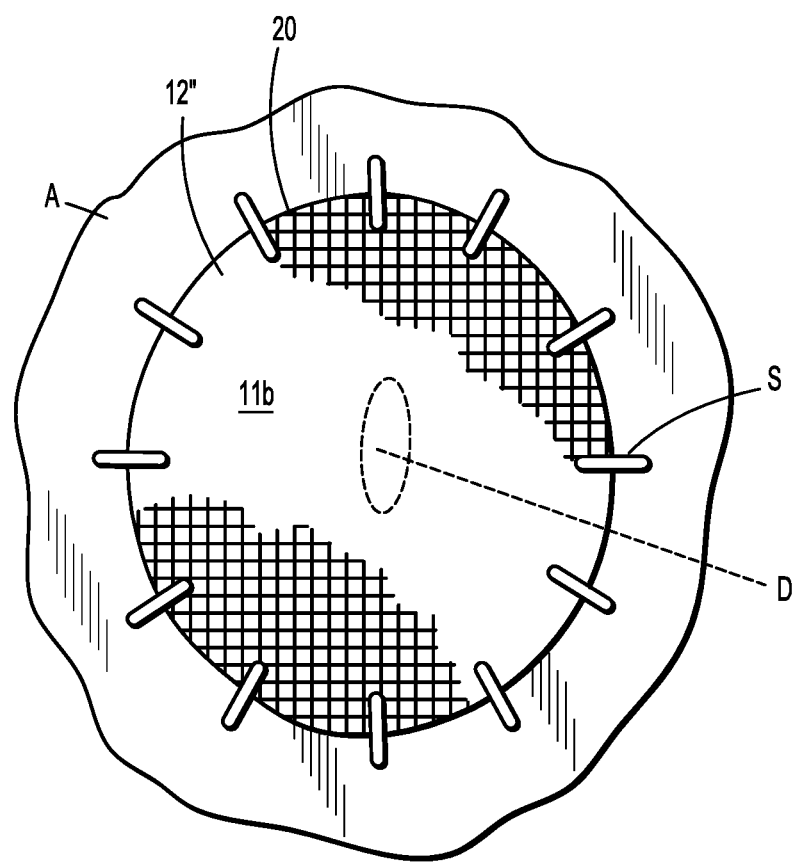
FIG. 11 is a top view of a surgical mesh in accordance with an embodiment of the present disclosure, shown secured to tissue via surgical staples.

With reference now to FIG. 11, an exemplary embodiment of a surgical implant of the present disclosure is discussed in terms of a surgical mesh. The surgical mesh may be used to reinforce tissue, and includes at least one sensing fiber for measuring a physiological parameter of the tissue and/or tissue environment. While the embodiment is directed to an abdominal wall hernia repair procedure, it is envisioned that the principles of the present disclosure are equally applicable to a range of soft tissue repair procedures, such as to the gall bladder, appendix, lungs, etc.

As shown in FIG. 11, a surgical mesh 11b includes a porous layer 12" having a fibrous structure including at least one sensing fiber 20. The surgical mesh 11b may have any shape, size, and/or dimension suitable for a particular surgical application, and is fabricated from biocompatible material(s) that may be porous, non-porous, or combinations thereof, as discussed above. In some embodiments, the fibrous structure of the surgical mesh 11b may be the same as, or similar to, surgical implant 10 (FIG. 1), and/or may include additional layers similar to, or the same as, surgical implant 10a (FIG. 2).

In embodiments, the sensing fiber 20 of the surgical mesh 11b is configured to measure a physiological parameter of interest related to monitoring conditions about a soft tissue defect, e.g., herniated tissue. In some embodiments, the sensing fiber 20 is a mechanical sensor, an electrical sensor, or an optical sensor adapted to measure a physical property of the tissue or the tissue environment. For example, the sensing fiber 20 may be configured to measure a load or force (e.g., strain) related to physical activity, such as intra-abdominal pressure, on a hernia repair site. As another example, the sensing fiber 20 may be configured to measure displacement of a surgical mesh indicative of mesh migration. In certain embodiments, the sensing fiber 20 is a strain gauge (e.g., an optical strain gauge).

In some embodiments, the sensing fiber 20 of the surgical mesh 11b is an optical sensor or a chemical sensor adapted to detect and/or quantify an amount of a material or substance (e.g., a chemical, an analyte, a byproduct, a metabolite, etc.) in tissue or the tissue environment indicative of a post-surgical condition or state. Accordingly, if the sensing fiber 20 detects the material or substance to be above or below a pre-determined value or to fall within a pre-defined range, a clinician and/or the patient is alerted so that a proper course of action may be taken to accelerate or optimize healing (e.g., to correct or balance the condition). For example, the sensing fiber 20 may be configured to measure nitrogen content as a biomarker for protein loss and/or muscle wasting such that if nitrogen levels fall below a pre-determined value, a clinician may administer an hGH treatment by, e.g., subcutaneous injection, to improve nitrogen balance and to maintain and/or increase muscle mass and/or strength.

The surgical mesh 11b may be introduced through a mesh deployment device and placed over damaged tissue (e.g., a tissue defect). Suitable devices include those shown and described, for example, in commonly owned U.S. Pat. No. 5,370,650, entitled "Articulating Mesh Deployment Apparatus," U.S. Pat. No. 8,317,808, entitled "Device and Method for Rolling and Inserting a Prosthetic Patch into a Body Cavity," U.S. Pat. No. 8,906,045, entitled "Articulating Patch Deployment Device and Method of Use," U.S. Pat. No. 9,107,726, entitled "Device and Method for Deploying and Attaching an Implant to a Biological Tissue," and U.S. Pat. No. 9,655,709, entitled "Mesh Deployment Devices and Kits," the entire contents of each of which is incorporated herein by this reference.

The surgical mesh 11b is secured to healthy tissue "A", such as an abdominal wall, surrounding a tissue defect "D" (shown in phantom) by fasteners "S" to anchor the surgical mesh 11b to the tissue "A". The fasteners "S" may be staples, sutures, tacks, anchors, among other fixation devices within the purview of those skilled in the art. The fasteners "S" may be retained within an end effector of a surgical fastener delivery device and deployed therefrom to secure the surgical mesh 11b to the tissue "A." Suitable fasteners and surgical fastener delivery devices include those shown and described, for example, in commonly owned U.S. Pat. No. 7,229,452, entitled "Tack and Tack Applier," U.S. Pat. No. 7,866,526, entitled "Apparatus for Applying Surgical Fasteners to Body Tissue," U.S. Pat. No. 8,216,272, entitled "Absorbable Anchor for Hernia Mesh Fixation," the entire contents of each of which is incorporated herein by this reference.

The surgical mesh 11b is secured to the tissue "A" to reinforce the tissue defect "D", as well as to allow a clinician to monitor properties around the tissue defect "D" via the sensing fiber(s) 20 of the surgical mesh 11b. As discussed above, the sensing fibers 20 transmit information to the clinician such that if a specific test criterion is met, a course of treatment may be selected, for example, to minimize or reduce patient morbidity and/or to detect or prevent postoperative repair failure.

Surgical instruments, such as the surgical staplers the mesh deployment devices, and the surgical fastener delivery devices, and the surgical implants usable therewith, described herein, may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Reference is made herein to U.S. Pat. No. 8,828,023 entitled "Medical Workstation," the entire content of which is incorporated herein by reference, for a more detailed discussion of the construction and operation of an exemplary robotic surgical system.

Persons skilled in the art will understand that the devices, systems, and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another exemplary embodiment without departing from the scope of the present disclosure, and that such modifications and variations are also intended to be included within the scope of the present disclosure. Accordingly, the subject matter of the present disclosure is not to be limited by what has been particularly shown and described.

What is claimed is:

1. A surgical system comprising:
an end effector including a plurality of fasteners; and
a surgical implant securable to tissue via the plurality of fasteners of the end effector, the surgical implant including at least one sensing fiber configured to measure a preselected physiological parameter, the at least one sensing fiber including a semiconducting element, an insulating element, and a plurality of conducting elements electrically connected in a circuit.

2. The surgical system according to claim 1, wherein the at least one sensing fiber of the surgical implant includes a core and a sheath disposed over the core.

3. The surgical system according to claim 2, wherein the core includes the semiconducting element, the plurality of conducting elements, and the insulating element.

4. The surgical system according to claim 2, wherein the core includes the semiconducting element and the plurality of conducting elements in contact with the semiconducting element.

5. The surgical system according to claim 1, wherein the surgical implant is a surgical buttress releasably attached to the end effector.

6. The surgical system according to claim 1, wherein the surgical implant is a surgical mesh including the at least one sensing fiber including a plurality of fibers.

7. The surgical system according to claim 1, wherein the plurality of conducting elements are electrodes.

8. The surgical system according to claim 1, further comprising a receiving unit in wireless communication with the at least one sensing fiber and configured to receive measurements of the preselected physiological parameter.

9. The surgical system according to claim 1, wherein the at least one sensing fiber is wireless and externally powered.

* * * * *